United States Patent [19]

Jacobson et al.

[11] Patent Number: 5,002,868
[45] Date of Patent: Mar. 26, 1991

[54] DNA SEQUENCING PROCESS USING STABLE ISOTOPES

[75] Inventors: K. Bruce Jacobson; Harold W. Schmitt, both of Anderson County, Tenn.

[73] Assignee: Atom Sciences, Inc., Oak Ridge, Tenn.

[21] Appl. No.: 221,734

[22] Filed: Jul. 20, 1988

[51] Int. Cl.$^5$ .................. C12Q 1/68; C07H 21/04; G01N 33/53

[52] U.S. Cl. .......................... 435/6; 435/91; 435/810; 436/501; 436/800; 436/803; 436/805; 536/27; 935/16; 935/17; 935/77; 935/78; 935/86; 935/88

[58] Field of Search .................. 435/6, 91, 810; 436/501, 800, 803, 805; 536/27; 935/16, 17, 77, 78, 86, 88

[56] References Cited

PUBLICATIONS

Prober et al. (1987), Science, vol. 238, pp. 336–341.

Primary Examiner—Robert A. Wax
Assistant Examiner—Ardin H. Marschel
Attorney, Agent, or Firm—Pitts and Brittian

[57] ABSTRACT

A DNA sequencing process using specific stable isotopes associated with specific terminators for labels. The process includes a step of incorporating a stable isotope in at least one of the deoxynucleoside triphosphates and/or the dideoxynucleoside triphosphates such that a terminated strand has included within it or at the end a stable isotope such as an isotope of sulphur. Replicated strands are then separated by performing gel electrophoresis thereon. The location of the DNA strand with the stable isotope assigned to a terminator is analyzed preferably by resonance ionization spectroscopy. The stable isotopes can be chosen such that specific labels are assigned to at least one, and preferably to each base, in the dideoxynucleoside triphosphates. In the preferred embodiment, each of the bases (A, T, G and C) are associated with a specific stable isotopic label, and can be analyzed in a single track which enhances the accuracy of the sequencing process.

9 Claims, 2 Drawing Sheets

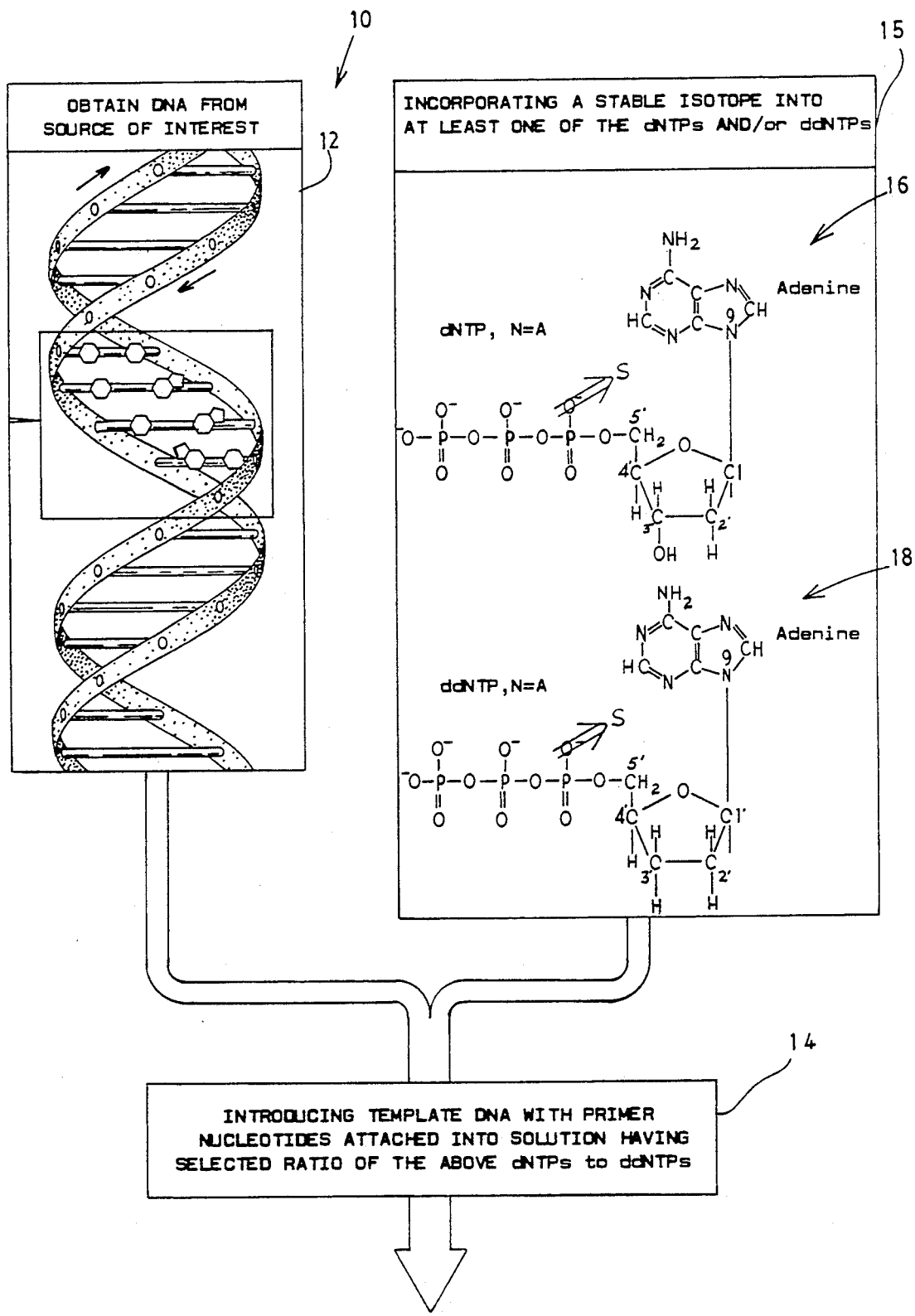

DNA SEQUENCING PROCESS USING STABLE ISOTOPES

DESCRIPTION

1. Technical Field

This invention relates to DNA sequencing, and more particularly concerns DNA sequencing using stable isotopes, rather than radioisotopes or fluorescent substances, to label the nucleotides in the DNA fragments.

2. Background Art

The nucleus of living cells possesses chromosomes which contain the genetic information necessary for the growth, regeneration and other functioning of organisms. Instructions concerning such functioning are contained in the molecules of deoxyribonucleic acid (DNA). DNA is within the chromosome in a form of complimentary strands commonly thought of as being configured in a double helix.

Genetic information in DNA is known to be contained within the sequence of nucleotides bases, deoxyribose and phosphate. The four bases consist of thymine (T), adenine (A), cytosine (C) and guanine (G). These bases can be joined between DNA strands only in accordance with well known pairing rules, i.e. T can only be joined with A, and C can only be joined with G. Accordingly, bases along one strand determine the order of bases along the complimentary strand.

Genetic information can be gathered by determining the sequence of nucleotides in DNA strands. Heretofore, DNA sequencing has been accomplished by obtaining DNA from a source of interest, and segregating a template DNA strand. A complimentary strand of DNA can then be synthesized by binding a primer oligonucleotide to the template strand. This template strand with the primer attached can then be introduced into a solution which can contain deoxynucleoside triphosphates, DNA polymerase, buffer and magnesium. Dideoxynucleoside triphosphates are usually introduced into the solution in a quantity having a preset ratio with respect to the deoxynucleoside triphosphate. It is known that dideoxynucleoside triphosphate serves as a deoxy terminating nucleotide (terminator) for the synthesized strands. Accordingly, replication termination occurs when the dideoxynucleoside triphosphate is incorporated into the replicated strand and this occurs at a frequency dependent upon the ratio of the deoxynucleoside triphosphates to the dideoxynucleoside triphosphates.

When numerous identical fragments of DNA are synthesized in such a solution, the dideoxynucleotides substitute randomly for the deoxynucleotides at different locations on the replicated or new strands. This results in DNA strands of various lengths, each terminating in a dideoxynucleotide. Where numerous strands are replicated in this manner, there is a high probability that each deoxynucleotide position will be occupied in a synthesized strand or fragment ending by a dideoxy.

These strands are then, in accordance with certain known techniques, subjected to polyacrylamide gel electrophoresis. This forces the strand under an electric field through a gel-like track. The shorter synthesized DNA strands move through the gel more quickly than the longer strands. Thus, the new DNA strands are separated by electrophoresis on a polyacrylamide gel such that a single nucleotide difference in length of new DNA strands is measured as a different migration distance.

Radioisotopes of $^{32}P$ or $^{35}S$ are usually incorporated in one or more deoxynucleoside triphosphates and/or dideoxynucleoside triphosphates to label the nucleotides in the newly synthesized strand. The fragments of DNA strands are produced when a dideoxy is substituted for each of the nucleotide types. The samples are then run in parallel on the gel and a pattern of bands can be obtained from which the base sequence can be read. In this regard, the placement of the new strand on an X-ray film produces images on the film that reveal where each dideoxy has been substituted in the new strands. The resulting films can then be placed in a side-by-side relationship to give the complete nucleotide sequence in four tracks or lanes.

While the above sequencing technique is capable of producing reliable results if properly applied, certain disadvantages are inherent in the process. For example, it is difficult to determine whether a given base is present when the film image is unclear. Also, anomalies can occur during the imaging process which can result in misread data. Further, radioisotopes are generally expensive, hazardous to personnel, and present waste disposal problems after use.

Accordingly, it is an object of the present invention to provide a DNA sequencing process which uses stable isotopes, rather than radioisotopes.

Another object of the present invention is to provide such a process in which all four specific base terminated DNA strands can be run in a single lane of electrophoresis gel.

Yet another object of the present invention is to use resonance ionization spectroscopy techniques for locating the stable isotopic label(s) substituted in the new strands.

Other objects and advantages of the process will become apparent upon reading the detailed description together with the drawings description as follows:

DISCLOSURE OF THE INVENTION

Figure 1:
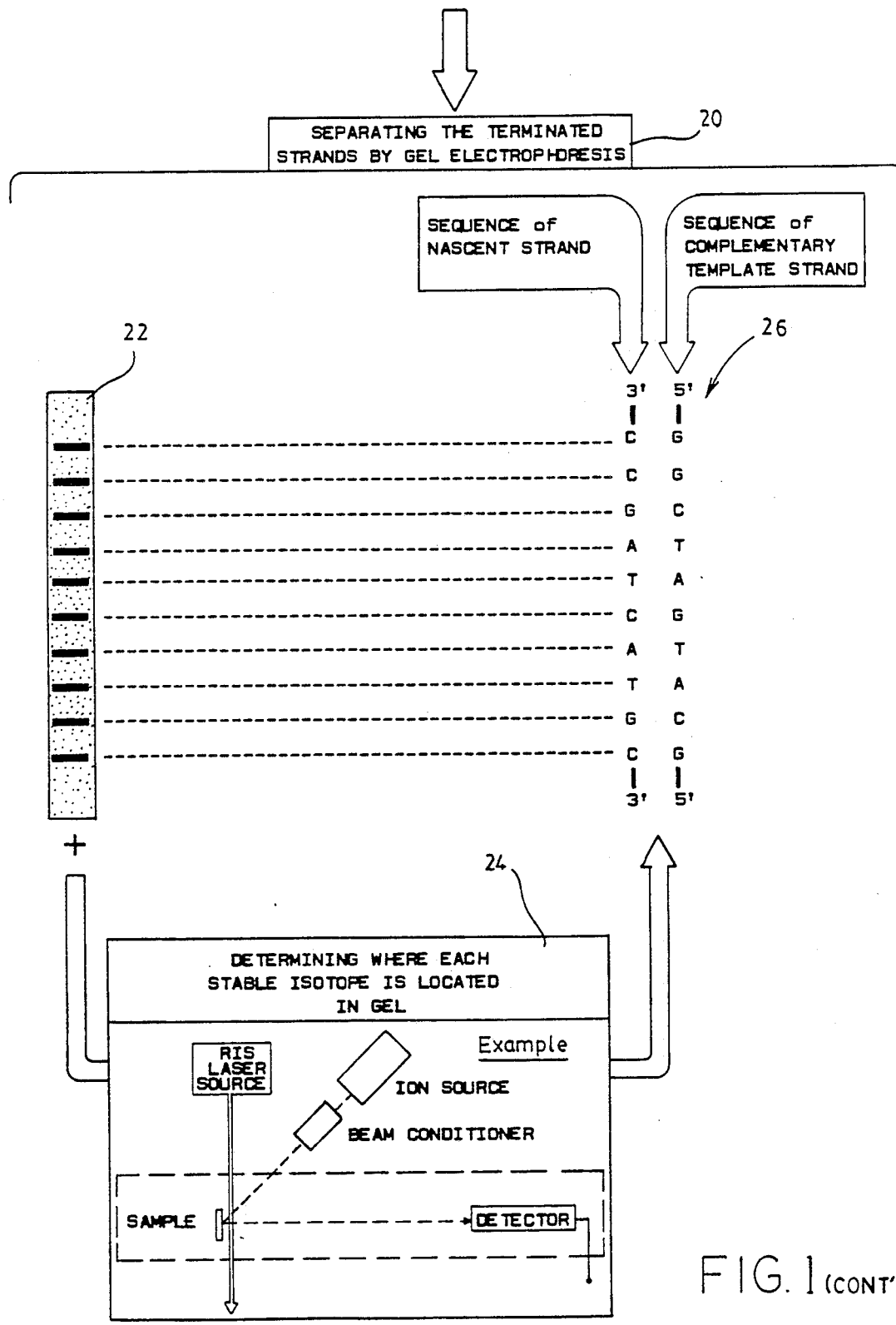
FIG. 1 illustrates a diagrammatic representation of the process of the present invention in which DNA sequencing is accomplished by using stable isotopes rather than radioisotopes. The figure also diagrammatically illustrates how the four specific base terminated DNA strands can be run in a single lane of electrophoresis gel. The incorporation of a stable isotope into an exemplary nucleotide adenine is shown on the first sheet of FIG. 1.

In accordance with various features of the present invention, a DNA sequencing process using stable isotopic labels is provided. The process includes the step of incorporating a stable isotope in one or more of the deoxynucleoside triphosphates and/or dideoxynucleoside triphosphates such that a terminated strand has a stable isotope, such as an isotope of sulphur, at its end or terminus. The replicated strands are then separated by performing gel electrophoresis thereon. The extent to which the stable isotopes have been substituted in the replicated strand and the location they occupy on the gel are analyzed preferably by resonance ionization spectroscopy. The stable isotopes can be chosen such that specific labels are given for at least one and preferably for each base in the dideoxynucleoside triphosphates. In the preferred embodiment, each of the bases (A, T, G and C) are associated with specific stable isotopic labels, and can be analyzed in a single track, thereby enhancing the accuracy of the sequencing process.

BEST MODE FOR CARRYING OUT THE INVENTION

A DNA sequencing process using a specific stable isotope associated with a specific terminator(s) is illustrated generally at 10 in FIG. 1. As indicated above, in the discussion of the background art, DNA sequencing has been accomplished by obtaining DNA from a source of interest as shown at 12, and segregating a template DNA strand. A complimentary strand of DNA can then be synthesized by binding a primer nucleotide to the template strand. This template strand with the primer attached can then be introduced into a solution containing normal deoxynucleoside triphosphates, DNA polymerase, buffer and magnesium as is shown diagrammatically at 14. Deoxynucleoside triphosphates (dNTPs, where N=A, T, G or C) are usually introduced into the solution in a ratio with a dideoxynucleoside triphosphates (ddNTPs, where N=A, T, G or C) which is preset. It is known that dideoxynucleoside triphosphate which serves as a deoxy terminating nucleotide for the synthesized strands is commonly referred to as a terminator. Accordingly, replication termination occurs when the dideoxynucleoside triphosphate is incorporated into the replicated strand; this occurs at a frequency dependent upon the ratio of the deoxynucleosides triphosphates to the dideoxynucleosides triphosphates.

When numerous identical fragments of DNA are synthesized in such a solution, the dideoxynucleotides substitute randomly for the deoxynucleotides at different locations on the strands. This results in DNA strands of various lengths, each terminating in a dideoxy or terminator, and there is a high probability that each deoxynucleotide position will be represented in a synthesized strand or fragment ending in a dideoxy.

These strands are then, in accordance with certain techniques, subjected to gel electrophoresis which forces the strands under an electric field through a gel like track. The shorter synthesized DNA strands move through the gel more quickly than the longer strands. Thus, the new DNA strands are separated by electrophoresis on a polyacrylamide gel such that a single nucleotide difference in length of new DNA strands is measured as a different migration distance.

In accordance with one feature of the present invention, a stable isotope is incorporated in at least one of the dNTPs or ddNTPs such that each new terminated strand has a stable isotope associated with an individual type of base on the ddNTP. This is shown at 15 in FIG. 1. The substitution of a sulphur isotope into deoxyadenine triphosphate (dATP) at 16 and into dideoxyadenosine triphosphate (ddATP) at 18. Of course, N can also equal G, T or C as is well known, and adenine (A) is shown as an example. Moreover, the stable isotope can be incorporated in an organic complex which in turn is incorporated into the dNTP or ddNTP and used as the label or tag for the different nucleotides.

In one embodiment, $^{32}S$, $^{33}S$, $^{34}S$, $^{36}S$ are used as the stable isotopes which are incorporated into the new strand of DNA that is a replica of the template DNA in which the sequence is to be determined. Using the well-known Sanger procedure (e.g., Sanger, F., Nicklen, S. and Collison, A. R. (1977) *Proc. Natl. Acad. Sci USA*, Vol. 74, No. 12, pp 5463-5467, December 1977, Biochemistry) to terminate the strand to give all possible lengths that terminate with a specific base, each of the four sulphur isotopes serve as labels specific to a given terminator. More specifically, for example, in one embodiment $^{32}S$ corresponds with a nucleotide having a base A, $^{33}S$ corresponds with base C, $^{34}S$ corresponds with base G, and $^{36}S$ corresponds with base T. This selection of tags or labels for a given base is arbitrary.

The replicated and terminated strands can then be separated by electrophoresis on a polyacryamide gel in a conventional manner is shown at 20. In accordance with the preferred embodiment of the present invention, each terminator is specific to a given sulphur isotope. Thus the sulphur isotopes serve as discrete labels that are associated with each base terminator or at least one base terminator if plural lanes are to be used. In this manner, the replicated strands can be superimposed and analyzed in a single track rather than running the samples in parallel on the gel as shown at 22.

The next step involves determining where each of the stable isotopes associated with terminators are located in the gel. To this end, means with suitable sensitivity to analyze the strands must be used. In the preferred embodiment, this is accomplished by analyzing the replicated strands with resonance ionization spectroscopy (RIS) as is shown at 24. This analysis technique has the sensitivity to perform the necessary determination of the location of a DNA strand in the polyacrylamide gel after electrophoresis. Details of RIS spectrometry can be found in U.S. Pat. No. 4,442,354, assigned to Atom Sciences, Inc., assignee of the present invention, and incorporated herein by reference. More specifically, resonance ionization spectrometry involves the known steps of bombarding the replicated strands of various lengths with energetic particles to produce a cloud of constituents from the isotopic nucleotides in DNA. The cloud is then subjected to a laser initiated resonance ionization spectroscopy for selectively ionizing constituents in the cloud corresponding to a particular component such as the isotopic sulphur. Ions resulting from the laser initiated resonance ionization spectroscopy are then accurately and substantially simultaneously detected as shown at 26 as a measure of the quantity of the component, isotopic sulphur, in the sample.

From the foregoing detailed description, it will be recognized by those skilled in the art that the present DNA sequencing process, which utilizes at least one and preferably four stable isotopes, allows for all four specific bases or base terminated DNA strands to be run in a single lane of electrophoresis gel in the preferred embodiment. The RIS analysis will sort out the isotopes and provides less error than normally produced by a comparison of four separate lanes utilizing known techniques. Further, high resolution is possible since RIS beams can be 10-100 μm. This allows the gel to be run for shorter times (distance) and for more information to be obtained from a standard 50-100 cm gel. Further, data from the RIS analysis can be displayed as bands which are comparable to X-ray film or as peaks and troughs which are comparable to dosimeters, or digitally. The sequence can also be printed out directly and any uncertainties designated. Also, the purchase and disposable of radioisotopes is eliminated and the process is safer for personnel.

It is, of course, understood that although a preferred embodiment of the invention has been illustrated and described, various modifications thereof will become apparent to those skilled in the art and, accordingly, the scope of the present invention should be defined only by the appended claims and equivalents thereof.

We claim:

1. A DNA sequencing process using individual stable isotopes that are associated with individual deoxynucleotides and/or terminators comprising the steps of:
   introducing template DNA strands with primer hybridization into a solution containing deoxynucleoside triphosphates (dNTP) having thymine, adenine, cytosine, and guanine bases; DNA polymerase; buffer; magnesium ion; and dideoxynucleoside triphosphate (ddNTP) wherein the ratio of dNTP to ddNTP is selected, said ddNTPs causing replication termination when incorporated into the replicated strand as dideoxynucleotide at a frequency dependent upon the ratio of dNTP to ddNTP;
   incorporating a specific stable isotope into at least one of the dNTPs and or ddNTPs such that a terminated strand has a specific stable isotope associated with each terminator at its end;
   separating the terminated strands by performing gel electrophoresis thereof; and
   determining where each said specific stable isotope is located on the gel.

2. A DNA sequencing process using stable isotopes associated with deoxynucleotides and/or terminators comprising the steps of:
   obtain DNA from a source of interest;
   segregating a template DNA strand;
   synthesizing a complementary strand of DNA by binding primer to the template strand;
   introducing template DNA strands with primer hybridization into a solution containing deoxynucleoside triphosphates (dNTP) having thymine, adenine, cytosine, and guanine bases; DNA polymerase; buffer; magnesium ion; and dideoxynucleoside triphosphate (ddNTPs) wherein the ratio of dNTP to ddNTP is selected, said ddNTPs causing replication termination when incorporated into the replicated strand as dideoxynucleoside phosphate at a frequency dependent upon the ratio of dNTP to ddNTP;
   incorporating a specific stable isotope of sulfur, wherein said specific isotope of sulphur is selected from a group consisting of $^{32}S$, $^{33}S$, $^{34}S$ and $^{36}S$, into at least one of the dNTPs and/or ddNTPs such that a terminated strand has a specific stable isotope of sulfur associated with the terminator at its end;
   separating the terminated strands by performing gel electrophoresis thereof; and
   determining where each said specific stable isotope of sulfur is located in the gel.

3. The DNA sequencing process of claim 1 wherein said specific stable isotope incorporated into at least one of the dNTPs and/or ddNTPs is a specific stable isotope of sulphur.

4. The DNA sequencing process of claim 2 wherein said specific stable isotope incorporated into at least one of the dNTPs and/or ddNTPs is a specific stable isotope of sulphur.

5. The DNA sequencing process of claim 1 wherein a separate specific stable sulphur isotope is incorporated into each type of dNTP and/or ddNTP such that each base type is labeled with a separate specific sulphur isotope.

6. The DNA sequencing process of claim 2 wherein a separate specific stable sulphur isotope is incorporated into each type of dNTP and/or ddNTP such that each base type is labeled with a separate specific sulphur isotope.

7. The DNA sequencing process of claim 4 wherein said specific sulphur isotope is selected from a group consisting of $^{32}S$, $^{33}S$, $^{34}S$ and $^{36}S$.

8. The DNA sequencing process of claim 1 wherein said step of determining where each said specific stable isotope that was assigned to a given terminator has been localized in said gel comprises analyzing said synthesized and terminated strands with resonance ionization spectroscopy.

9. The DNA sequencing process of claim 2 wherein said step of determining where each said specific stable isotope that was assigned to a given terminator has been localized in said gel comprises analyzing said synthesized and terminated strands with resonance ionization spectroscopy.

* * * * *